United States Patent

Vu et al.

[11] Patent Number: 5,939,055
[45] Date of Patent: Aug. 17, 1999

[54] CLEAR ANTIPERSPIRANT STICK CONTAINING DIBENZYLIDENE ALDITOL

[75] Inventors: Tuan M. Vu, Canton; Carl F. Iovanni, Cambridge; Jayant N. Sane, Framingham, all of Mass.

[73] Assignee: The Gillette Company, Boston, Mass.

[*] Notice: This patent is subject to a terminal disclaimer.

[21] Appl. No.: 08/913,739

[22] PCT Filed: Feb. 29, 1996

[86] PCT No.: PCT/US96/02836

§ 371 Date: Apr. 14, 1998

§ 102(e) Date: Apr. 14, 1998

[87] PCT Pub. No.: WO96/26709

PCT Pub. Date: Sep. 6, 1996

[51] Int. Cl.$^6$ .............................. A61K 7/37; A61K 7/34; A61K 7/38; A61K 7/00

[52] U.S. Cl. .................. 424/65; 424/66; 424/68; 424/400; 424/401; 424/DIG. 5

[58] Field of Search .................. 424/65, 66, 68, 424/400, 401, DIG. 5

[56] References Cited

U.S. PATENT DOCUMENTS

| | | | |
|---|---|---|---|
| H1473 | 8/1995 | Orofino et al. | 424/27 |
| 3,981,986 | 9/1976 | Rubino | 424/47 |
| 4,017,599 | 4/1977 | Rubino | 424/47 |
| 4,154,816 | 5/1979 | Roehl et al. | 424/68 |
| 4,346,079 | 8/1982 | Roehl | 424/65 |
| 4,383,988 | 5/1983 | Teng et al. | 424/68 |
| 4,518,582 | 5/1985 | Schamper et al. | 424/66 |
| 4,719,102 | 1/1988 | Randhawa et al. | 424/66 |
| 4,720,381 | 1/1988 | Schamper et al. | 424/66 |
| 4,722,835 | 2/1988 | Schamper et al. | 424/66 |
| 4,725,430 | 2/1988 | Schamper et al. | 424/66 |
| 4,743,444 | 5/1988 | McCall | 424/65 |
| 4,781,917 | 11/1988 | Luebbe et al. | 424/65 |
| 4,816,261 | 3/1989 | Luebbe et al. | 424/65 |
| 4,822,602 | 4/1989 | Sabateili | 424/65 |
| 4,948,578 | 8/1990 | Burger et al. | 424/65 |
| 4,954,333 | 9/1990 | Ward | 424/65 |
| 5,106,999 | 4/1992 | Gardlik et al. | 549/68 |
| 5,162,378 | 11/1992 | Guthauser | 514/66 |
| 5,200,174 | 4/1993 | Gardlik et al. | 424/364 |
| 5,270,034 | 12/1993 | Cheng | 424/785 |
| 5,286,755 | 2/1994 | Kauffmann et al. | 514/66 |
| 5,346,694 | 9/1994 | Juneja | 424/68 |
| 5,368,848 | 11/1994 | Brazinsky et al. | 424/944 |
| 5,376,363 | 12/1994 | Benfatto et al. | 424/66 |
| 5,405,605 | 4/1995 | Shin | 424/65 |
| 5,463,098 | 10/1995 | Giovanniello et al. | 556/66 |
| 5,490,979 | 2/1996 | Kasat et al. | 424/68 |
| 5,516,511 | 5/1996 | Motley et al. | 424/66 |
| 5,520,907 | 5/1996 | Orogino et al. | 424/65 |
| 5,585,092 | 12/1996 | Trandai | 424/65 |
| 5,705,171 | 1/1998 | Iovanni et al. | 424/401 |
| 5,725,846 | 3/1998 | Vu et al. | 424/65 |

FOREIGN PATENT DOCUMENTS

| | | |
|---|---|---|
| 0260030 | 3/1988 | European Pat. Off. . |
| 0 260 030 B1 | 6/1988 | European Pat. Off. . |
| 0 404 532 A1 | 12/1990 | European Pat. Off. . |
| 0451002 | 10/1991 | European Pat. Off. . |
| 0 599 775 A1 | 6/1994 | European Pat. Off. . |
| WO 91/15191 | 10/1991 | WIPO . |

OTHER PUBLICATIONS

Klepak, "Antiperspirants take a clear lead", *Manufacturing Chemist* (Nov. 1994), pp. 31–36.
Disorbene, Roquette product brochure (1992).
The Merck Index (9$^{th}$ ed. 1976), p.778 (No. 5825).
Schwarzenbach, Complexometric Titrations (2nd English ed., 1969), pp. 145–155, 268–269.

*Primary Examiner*—Shelley A. Dodson
*Attorney, Agent, or Firm*—Stephan P. Williams

[57] ABSTRACT

A clear gel cosmetic stick is disclosed which includes a liquid vehicle, an antiperspirant salt dissolved in the liquid vehicle, a dibenzylidene alditol, and a co-gellant. The co-gellant is preferably a hydroxyalkyl cellulose and the stick optionally also includes a chelating agent. The cosmetic stick comprises in percent by weight about 70% to about 95%, preferably 75 to 92%, of a liquid vehicle, about 1% to about 22%, preferably 3% to 15%, of an antiperspirant salt dissolved in the vehicle, about 0.5% to about 2% of a dibenzylidene alditol, about 0.1% to about 0.5%, preferably 0.2% to 0.4%, of a hydroxyalkyl cellulose, and optionally about 0.05% to about 3%, preferably 0.1% to 2%, of a chelating agent. Preferably the liquid vehicle comprises a polyhydric alcohol having from 3 to 6 carbon atoms and from 2 to 6 hydroxyl groups and is substantially free of monohydric alcohol and strong alkali such as sodium hydroxide and potassium hydroxide. Preferably the cosmetic stick will have a turbidity of less than about 120 NTU, more preferably less than 100 NTU, and a hardness of about 60 to 150.

17 Claims, No Drawings

CLEAR ANTIPERSPIRANT STICK CONTAINING DIBENZYLIDENE ALDITOL

This application is a 371 of application PCT/US96/02836, which is a continuation-in-part of application Ser. No. 08/588,618 filed on Feb. 6, 1996, now U.S. Pat. No. 5,725,846, and a continuation-in-part of application Ser. No. 08/397,450 filed on Mar. 2, 1995, now abandoned, which application was re-filed as application Ser. No. 08/695,839 on Jul. 10, 1996, now U.S. Pat. No. 5,705,171.

The invention relates to clear gel cosmetic sticks which include a solubilized antiperspirant salt.

Gel antiperspirant sticks typically include a liquid vehicle, an antiperspirant salt, a gelling agent, and one or more emollients. Dibenzylidene alditols like dibenzylidene sorbitol (DBS), also known as dibenzylidene monosorbitol acetal (DBMSA), are one type of gelling agent that has been used in such sticks. Dibenzylidene alditols may degrade during manufacture and subsequent storage of the gel stick, in part because of the presence of the acidic antiperspirant salt in the stick. One product of the degradation, benzaldehyde, can provide an undesirable odor and can cause the stick to lose hardness and to become discolored. Commercially available DBS gel antiperspirant sticks generally contain more than 2% DBS in order to have sufficient hardness. However, such sticks do not have optimum clarity or odor characteristics.

Various stabilizing agents have been incorporated into gel antiperspirant sticks containing dibenzylidene alditols in an effort to minimize dibenzylidene alditol degradation. Examples include sodium hydroxide, potassium hydroxide, sodium carbonate, zinc acetate, zinc oxide, zinc carbonate, potassium carbonate, diethanolamine, triethanolamine, disodium succinate, sodium benzoate, sodium octanoate, hexamethylenetetramine, urea, 2-amino-2-methyl-1-propanol, magnesium sulfate, calcium hydroxide, and N-(2-hydroxyethyl) acetamide. These and other stabilizing agents, although apparently effective to some degree in stabilizing the dibenzylidene alditol, may have other problems associated with them. Sodium hydroxide and potassium hydroxide, for example, may provide a composition with an undesirable odor.

The invention features a clear gel cosmetic stick which includes a liquid vehicle, an antiperspirant salt dissolved in the liquid vehicle, and a dibenzylidene alditol, and is further characterized in that said stick includes a hydroxyalkyl cellulose or a chelating agent or both a hydroxyalkyl cellulose and a chelating agent. The cosmetic stick comprises in percent by weight about 70% to about 95%, preferably 75% to 92%, of a liquid vehicle, about 1% to about 22%, preferably 3% to 15%, of an antiperspirant salt dissolved in said vehicle, about 0.5% to about 3%, preferably 0.5% to 1.5%, of a dibenzylidene alditol, about 0.1% to about 0.5%, preferably 0.2% to 0.4%, of a hydroxyalkyl cellulose, and about 0.05% to about 3%, preferably 0.1% to 2%, of a chelating agent. Preferably the liquid vehicle comprises a polyhydric alcohol having from 3 to 6 carbon atoms and from 2 to 6 hydroxyl groups and is substantially free of monohydric alcohol and strong alkali such as sodium hydroxide and potassium hydroxide. Preferably the cosmetic stick will have a pH greater than 4.4, more preferably greater than 4.7, a turbidity of less than about 120 NTU, more preferably less than 100 NTU, and a hardness of about 60 to 150. By lowering the dibenzylidene alditol level to 1.5% or lower, the clarity and odor characteristics of the stick are greatly improved. The hardness of the stick is maintained by the addition of the hydroxyalkyl cellulose. The color of the stick is improved by the addition of the chelating agent.

A "clearing" gel stick, as used herein, is a stick that is visually clear so that, like glass, it allows ready viewing of objects behind it. Preferred clear gel sticks have a turbidity measurement, expressed in Nephelometric Turbidity Units (NTU) of less than 120 NTU, more preferably less than 100 NTU, and most preferably less than 80 NTU, when measured with a Hellige #965 Direct-Reading Turbidimeter. By "substantially free of off-odor" is meant that the gel stick (without any fragrance or fragrance masking agent) has an off-odor rating of 0 to 2, preferably 0 to 1, on a scale of 0 to 5 used by trained odor (or perfumery) experts, where 0 signifies no detectable off-odor and a rating of 4 to 5 is deemed unacceptable odor. By "stable" is meant that samples of the product, when stored at 45° C. for three months, will not exhibit any noticeable benzaldehyde odor or other off-odor (i.e. retains an odor rating of 0 to 2) and will not exhibit any significant change in clarity (i.e. retains a clarity of better than 120 NTU). Yellowness is measured by spectrophotometer absorbance at 408 nm with 0 corresponding to 0 ppm ferric chloride in water and 5 corresponding to 500 ppm ferric chloride in water.

The preferred clear gel sticks include a liquid vehicle, an antiperspirant salt dissolved in the liquid vehicle and a dibenzylidene alditol gelling agent. The liquid vehicle along with the gelling agent provide the matrix, or body, of the gel stick.

The preferred liquid vehicle comprises a polyhydric alcohol having from 3 to 6 carbon atoms and from 2 to 6 hydroxyl groups. Such polyhydric alcohols include diethylene glycol, triethylene glycol, dipropylene glycol, 1,2-propylene glycol, 1,3-propylene glycol, 2-methyl-1,3-propanediol, 1,4-butylene glycol, 1,2-butylene glycol, 1,3-butylene glycol, 2,3-butylene glycol, 2,4-dihydroxy-2-methylpentane, glycerin, sorbitol and the like, and mixtures thereof. Preferred are 1,2-propylene glycol (normally referred to simply as propylene glycol), dipropylene glycol, 2-methyl-1,3-propanediol, 1,3-butylene glycol, sorbitol and mixtures thereof. Most preferred as the liquid vehicle is propylene glycol, which may optionally include one or more of the aforementioned polyhydric alcohols. While the liquid vehicle may optionally include a monohydric alcohol such as ethanol, it is preferred that the liquid vehicle be substantially free of monohydric alcohol. While the liquid vehicle may also optionally contain a co-solvent for the gelling agent (e.g. N-methyl pyrrolidone), as described in the prior art, such is not preferred.

The gel stick generally includes between about 70% and about 95%, preferably between about 75% and about 92%, of the liquid vehicle by weight. A stick including an insufficient quantity of the liquid vehicle may be unclear or may provide an inadequate support matrix for the remainder of the components. A stick including too much liquid vehicle may lack sufficient quantities of one or more of the other stick components.

The dibenzylidene alditol is the gelling agent. Examples include dibenzylidene sorbitol (DBS), dibenzylidene xylitol, and dibenzylidene ribitol. The aromatic rings in each benzylidene group may be unsubstituted or substituted, as described in U.S. Pat. No. 5,200,174, which is incorporated herein by reference. When substituted, it is preferred that the benzyl ring contain an electron withdrawing group at the meta position. Typical substituted compounds include di(meta-fluorobenzylidene) sorbitol and di(metachlorobenzylidene) sorbitol. The preferred gelling agent is dibenzylidene sorbitol (DBS).

The gel stick may contain between about 0.1% and about 5%, preferably between about 0.5% and about 3%, of the dibenzylidene alditol by weight. If the gel stick includes too much of the dibenzylidene alditol, it may lack sufficient clarity and/or may have an undesirable odor. If the gel stick includes too little of the dibenzylidene alditol it may lack sufficient hardness. For optimum clarity the gel stick should preferably contain 0.5% to 2%, more preferably 0.5% to 1.5%, most preferably 0.7% to 1.3%, of the dibenzylidene alditol by weight. A particularly advantageous feature of the present invention is the use of low levels (i.e. 1.5% or less) of the dibenzylidene alditol gelling agent, which results in sticks of exceptional clarity and odor-free characteristics.

Antiperspirant salts which may be used in the gel sticks of the present invention include any of the conventional aluminum, zirconium and aluminum-zirconium salts known to be useful in antiperspirant compositions. These salts include aluminum halides and aluminum hydroxy halides (e.g., aluminum chlorohydrate), and mixtures or complexes thereof with zirconyl oxyhalides and zirconyl hydroxyhalides (e.g. aluminum-zirconium chlorohydrate).

Preferred aluminum salts are those having the general formula $Al_2(OH)_{6-a}X_a$ wherein X is Cl, Br, I or $NO_3$, and a is about 0.3 to about 4, preferably about 1 to 2, such that the Al to X mole ratio is about 1:1 to 2.1:1. These salts generally have some water of hydration associated with them, typically on the order of 1 to 6 moles per mole of salt. Most preferably, the aluminum salt is aluminum chlorohydrate (i.e. X is Cl) and a is about 1, such that the aluminum to chlorine mole ratio is about 1.9:1 to 2.1:1.

Preferred aluminum-zirconium salts are mixtures or complexes of the above-described aluminum salts with zirconium salts of the formula $ZrO(OH)_{2-pb}Y_b$ wherein Y is Cl, Br, I, $NO_3$, or $SO_4$, b is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $ZrO(OH)_{2-b}Cl_b$ wherein b is about 1 to 2, preferably about 1.2 to about 1.9. The preferred aluminum-zirconium salts have an Al:Zr ratio of about 1.7 to about 12.5, most preferably about 2 to about 10, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. The aluminum-zirconium salt complexes may also contain a neutral amino acid, preferably glycine, typically with a Gly:Zr ratio of about 1:1 to 4:1.

It is especially preferred to utilize enhanced efficacy aluminum and aluminum-zirconium antiperspirant salts in the gel sticks of the present invention. By "enhanced efficacy antiperspirant salt" is meant antiperspirant salts which, when reconstituted as 10% aqueous solutions, produce an HPLC chromatogram (as described, for example, in U.S. Pat. No. 5,330,751, which is incorporated herein by reference) wherein at least 70%, preferably at least 80%, of the aluminum is contained in two successive peaks, conveniently labeled peaks 3 and 4, wherein the ratio of the area under peak 4 to the area under peak 3 is at least 0.5, preferably at least 0.7, and most preferably at least 0.9 or higher. Any suitable HPLC technique may be employed provided that it is capable of resolving the Al component into five peaks. The enhanced efficacy (or activated) antiperspirant salts are well-known in the industry and are commercially available from several suppliers.

To incorporate the antiperspirant salt in the gel stick composition, it is preferred that the salt is first solubilized or dissolved in a portion of the liquid vehicle. Accordingly, it is preferred to utilize polyhydric alcohol solutions of antiperspirant salts. Especially preferred are solubilized salts which have been partially neutralized by addition of a pH-raising agent to a pH of about 4.1 to 5.0, preferably about 4.3 to 4.8. Particularly preferred neutralized antiperspirant salts are those which contain an additional alkaline glycinate, such as sodium, potassium, or zinc glycinate. Such solubilized antiperspirant salts are described in U.S. Pat. No. 5,723,135, and in U.S. Pat. No. 5,463,098, the disclosures of which are incorporated herein by reference. An example of such a solubilized salt, which is partially neutralized with zinc glycinate, is Westchlor A2Z 8106 (Westwood Chemical Corp.). The preparation of a preferred solubilized antiperspirant salt is described in Example 1 below.

The additional alkaline glycinate which is preferably included in the solubilized antiperspirant salt raises the pH of the antiperspirant salt and, as a result, reduces the degradation of the dibenzylidene alditol in the gel stick. It is generally preferred to add sufficient alkaline glycinate to the solubilized antiperspirant salt so as to raise the pH of an approximately 10% aqueous solution of the antiperspirant salt to about 4.1 to 5.0, preferably about 4.3 to 4.8. (The 10% aqueous solution may be an approximately 50:50 polyhydric alcohol:water solution.) Preferred gel sticks which include such a partially neutralized salt will have a pH greater than 4.4, preferably about 4.7 to about 5.5, and more preferably about 4.8 to about 5.3. The pH of the finished stick can be measured by dissolving one part stick in ninety-nine parts water. The pH of the solubilized antiperspirant salt or of the resulting stick can, of course, be adjusted to the aforementioned preferred pH ranges with any pH-raising agent, or combination of pH-raising agents, provided that the agent or agents selected are soluble in the vehicle and do not adversely affect the clarity or odor characteristics of the stick to a significant extent.

Sufficient antiperspirant salt should be dissolved in the liquid vehicle so that the final composition, after all components are added, includes between about 1% and about 22%, preferably between about 3% and about 15%, of the antiperspirant salt by weight. It should be noted that reference throughout this application to weight percent of antiperspirant salt is intended to be calculated in accordance with the standard industry method, which includes bound water and glycine. This calculation compares with the new U.S.P. method, which excludes bound water and glycine, as follows:

| SALT | STANDARD METHOD | USP METHOD |
|---|---|---|
| Al—Zr—Gly in Prop. Glycol (Ex. 1) | 30% | 22% |
| Al—Zr—Gly in stick (Ex. 2) | 11% | 8.6% |

The gel stick will also optionally and preferably include a hydroxyalkyl cellulose as an additional gelling agent (or co-gellant). The hydroxyalkyl cellulose provides the stick with adequate hardness even when the stick includes only a low level of the dibenzylidene alditol. The combined use of the hydroxyalkyl cellulose co-gellant with reduced amounts of the dibenzylidene alditol (i.e. amounts of 1.5% or less) enable the production of gel sticks of exceptional clarity and stability. The preferred hydroxyalkyl cellulose co-gellants include alkyl groups with between one and five carbon atoms. The preferred co-gellant is hydroxypropylcellulose (e.g. Klucel HFF, Aqualon). When included in the gel stick, the hydroxyalkyl cellulose will be present in an amount of about 0.08% to 1%, preferably 0.1% to 0.5%, more preferably 0.2% to 0.4%, by weight.

Preferred gel sticks have a hardness of between about 60 and about 150 when measured on a TA-XT2 Texture Analyzer (Stable Micro System, Haste Hill, England). These hardness measurements correlate to the grams of force required for the standard arrowhead-type penetration needle to penetrate the stick a distance of 5 mm at 1 mm per second.

The gel stick of the present invention will also optionally and preferably include a chelating agent to improve its color and clarity. A chelating agent is a compound in which atoms form more than one coordinate bond with metals in solution. Examples of chelating agents include salts of ethylenediamine-tetraacetic acid (EDTA) such as tetrasodium and trisodium ethylonediaminetetraacetate ($Na_4EDTA$ and $Na_3EDTA$), hydroxyethylethylenediaminetriacetate (HEDTA), diethylenetriaminepentaacetate (DTPA), nitrilotriacetate (NTA), othanoldiglycine disodium salt (EDG), diethanolglycine sodium salt (DEG), and 1,3-propylenediaminetetraacetic acid (PDTA). All of these are known and commercially available. Preferred chelating agents include tetrasodium and trisodium ethylenediaminetetraacetate ($Na_4EDTA$ and $Na_3EDTA$). The gel sticks generally include between about 0.05% and about 3%, preferably between about 0.1% and about 2%, of the chelating agent by weight. If too little chelating agent is included, the stick may have less clarity, an undesirable odor, and/or undesirable yellowness. If too much chelating agent is included, the clarity and/or other properties of the stick may be adversely affected. The chelating agent may reduce the color (in particular the yellow color) of the stick that can result, for example, from the presence of residual iron (or other metal contaminants) that may be present in the stick from a variety of sources. The gel stick preferably measures 0–1 on the yellowness scale.

The chelating agent may also act as a gelling agent stabilizer by increasing the pH of the stick, thus reducing or eliminating the need for other alkaline gelling agent stabilizers such as NaOH and KOH. The gel stick preferably is substantially free of NaOH and KOH and, as a result, does not have the odor that can result from the interaction of these materials with the vehicle, particularly with propylene glycol. The elimination of other alkaline gelling agent stabilizers, particularly NaOH and KOH, is an advantageous feature of the present invention and is believed to substantially contribute to the odor-free characteristics of the gel sticks of the present invention.

Suitable emollients may be incorporated into the gel stick to provide it with desirable application properties (smoothness, reduced tack, etc.). Examples of emollients include fatty acid esters such as isopropyl myristate and isopropyl palmitate; diesters of adipic, phthalic, and sebacic acids such as di-n-butyl phthalate, diisopropyl sebacate, diethyl sebacate, and diisopropyl adipate; propylene glycol diesters of short chain fatty acids; nonvolatile silicone oils such as dimethyl siloxane and dimethicone copolyol; volatile silicones such as Dow Corning 344 and Dow Corning 345 (available from Dow Corning), Silicone 7207 and Silicare 7158 (available from Union Carbide), and SF 1202 (available from General Electric); $C_{12}$–$C_{15}$ alcohol benzoates such as Finsolv (available from Finetex, Inc.); fatty alcohols such acetyl alcohol and stearyl alcohol; alkyl ether derivatives of polyethylene glycols, polypropylene glycols and polypropylene polyethylene glycol copolymers such as PPG-5-Buteth-7, PPG-5-Ceteth-20, PPG-3-Isosteareth-9 and Glycereth-7-Diisononanoate. Many other examples of emollients are known in the art. The gel stick should include a sufficient quantity of emollient to provide the stick with the desired application properties without interfering with the clarity of the product. The preferred emollients should be soluble in the liquid vehicle and form a clear solution therein. The gel stick preferably includes less than about 10%, more preferably less than about 3%, and most preferably between about 0.25% and 1.25%, of emollients by weight.

The fragrances used in the gel stick can be any conventional fragrance that provides the stick with a desired scent. The quantity of fragrance included should be the quantity needed to provide the desired scent. The gel stick generally includes less than about 2.5%, preferably less than about 1.5%, of the fragrance by weight.

The gel stick may contain other optional conventional ingredients such as humectants, hardeners, fillers, colorants, preservatives, bacteriocides, UV absorbers, and the like. Obviously such materials should be selected so as not to adversely affect the clarity of the stick.

The gel sticks of the present invention may be prepared by the conventional two-phase procedure known in the art. That is, a first phase containing a portion of the vehicle and the gelling agent is heated to a temperature sufficient to dissolve the gelling agent (typically about 110° C.), then cooled to about 100° C. A second phase containing a portion of the vehicle and the remaining ingredients is prepared and heated to about 60 to 80° C., then combined with the first phase. The combined mixture is poured into stick form molds and cooled to solidify. A preferred alternative method of preparation is to combine all of the ingredients at a temperature of less than 50° C. with sufficient mixing to form a uniform dispersion (the dibenzylidene alditol is not soluble at low temperature; the hydroxyalkyl cellulose, if present, may be predissolved in a portion of the vehicle prior to blending). Portions of this dispersion are then flash heated to a temperature sufficient to dissolve the dibenzylidene alditol, then the resulting solution is poured into stick form molds and cooled to solidify. Ideally, no portion of the solution will be kept at a temperature in excess of 90° C. for more than a few minutes. This preferred process is described more fully in U.S. Pat. No. 5,723,135, the disclosure of which is incorporated herein by reference.

The following specific examples further illustrate the invention:

EXAMPLE 1—Antiperspirant Salt

A 50% sodium glycinate solution was prepared by mixing 171 lbs. (77.6 kg) 50% NaOH with 67.8 lbs. (30.8 kg) water, then adding 160.3 lbs (72.8 kg) of glycine (1:1 mole ratio of glycine to NaOH), the temperature rising from 25° to 30° C., then from 30° to 35° C., after the first and second additions respectively. To 103.3 lbs. (46.9 kg) of propylene glycol was added 7.8 lbs. (3.5 kg) of 50% sodium glycinate and the solution mixed for ten minutes. To this solution was added 33.9 lbs. (15.4 kg) of zirconium hydroxychloride glycinate (50% aqueous ZHC-gly solution with a Zr:gly ratio of about 1:1). After mixing this solution for about ten minutes, 255 lbs. (115.8 kg) of 10% ACH' solution (prepared by heating 10% ACH at about 80° C. for about 16 to 17 hours) was added and mixed for about ten minutes. This solution was preheated to about 70° to 75° C. and fed continuously to a type JHE flash evaporator (APV Crepaco Inc., Tonawanda, N.Y.; evaporator modified by mounting to the top of the flash chamber a 3 foot rectification tower filled with about 2.5 feet of 0.5 inch ceramic Berl saddles) maintained at about 60 mm Hg (absolute pressure) from which was withdrawn at about 1 gal/hr a clear solution comprising 65% propylene glycol, 30% enhanced efficacy aluminum-zirconium tetrachlorohydrate-glycine (more than 80% of aluminum in peaks 3 and 4 with peak 4 to peak 3 area ratio greater than 1 and Gly:Zr ratio about 1.6:1), and 5% water. The pH of a sample of this solution diluted with an equal portion of distilled water was about 4.7. This antiperspirant salt solution is incorporated into the following examples.

EXAMPLES 2 AND 3

| Ingredient | Ex. 2 Wt. % | Ex. 3 Wt. % |
| --- | --- | --- |
| Propylene glycol | 85.50 | 84.70 |
| Al/Zr tetrachlorohydrate-gly | 11.00* | 11.00* |
| Dibenzylidene sorbitol | 1.00 | 1.30 |
| Hydroxypropyl cellulose | 0.30 | 0.30 |
| Na₄EDTA | 0.20 | 0.20 |
| Diisopropyl sebacate | — | 1.00 |
| Glycereth-7-diisononanoate | 0.50 | — |
| Dimethicone copolyol (ABIL B 8851) | 0.25 | 0.25 |
| Fragrance | 1.25 | 1.25 |

*Weight % of salt in final composition. Salt is added in solubilized form as prepared in Example 1.

Examples 2 and 3 were prepared according to the following procedure.

Phase A:

About 65% of the total propylene glycol mass (excluding that which is part of the antiperspirant salt solution) is added to an appropriately sized vessel. Hydroxypropyl cellulose is added and stirred well to dissolve. After heating this solution to 110°–115° C., the dibenzylidine sorbitol is added with stirring until completely dissolved. This Phase A solution is then cooled to about 100° C.

Phase B:

About 35% of the total propylene glycol mass (excluding that which is part of the antiperspirant salt solution) is added to an appropriately sized vessel, stirred and heated to about 60–70° C. The Na₄EDTA is added and mixed well. The Al/Zr tetrachlorohydrate-gly solution (as prepared in Example 1) is added and the solution mixed well until it becomes clear and homogeneous. The emollients (i.e. diisopropyl sebacate or glycereth-7-diisononanoate and the dimethicone copolyol) are then added and the Phase B solution is mixed well until clear.

Combined Phase:

Phase B is added to Phase A with mixing and cooled to about 80° C. The fragrance is added and allowed to mix well. The product is poured into suitable stick containers and cooled to solidify.

EXAMPLES 4 AND 5

| Ingredient | Ex. 4 Wt. % | Ex. 5 Wt. % |
| --- | --- | --- |
| Propylene glycol | 86.00 | 85.65 |
| Al/Zr tetrachlorohydrate-gly | 11.00* | 11.00* |
| Dibenzylidene sorbitol | 0.50 | 0.95 |
| Hydroxypropyl cellulose | 0.30 | 0.30 |
| Na₄EDTA | 0.20 | 0.20 |
| Glycereth-7-diisononanoate | 0.50 | 0.50 |
| Dimethicone copolyol (ABIL B 8851) | 0.25 | 0.25 |
| Fragrance | 1.25 | 1.25 |

*Weight % of salt in final composition. Salt is added in solubilized form as prepared in Example 1.

Examples 4 and 5 are prepared by procedures analogous to the procedure used to prepare Examples 2 and 3.

| Ingredient | Ex. 6 Wt. % | Ex. 7 Wt. % |
| --- | --- | --- |
| Propylene glycol | 85.00 | 84.80 |
| Al/Zr tetrachlorohydrate-gly | 11.00* | 11.00* |
| Dibenzylidene sorbitol | 1.20 | 1.50 |
| Hydroxypropyl cellulose | 0.30 | — |
| Na₄EDTA | — | 0.20 |
| Diisopropyl sebacate | 1.00 | 1.00 |
| Dimethicone copolyol (ABIL B 8851) | 0.25 | 0.25 |
| Fragrance | 1.25 | 1.25 |

*Weight % of salt in final composition. Salt is added in solubilized form as prepared in Example 1.

* Weight % of salt in final composition. Salt is added in solubilized form as prepared in Example 1.

Examples 6 and 7 are prepared by a procedure analogous to the procedure used to prepare Examples 2 and 3.

| Ingredient | Wt. % |
| --- | --- |
| Propylene glycol | 84.85 |
| Al/Zr tetrachlorohydrate-gly | 11.00* |
| Dibenzylidene sorbitol | 1.10 |
| Hydroxypropyl cellulose | 0.35 |
| Na₄EDTA | 0.20 |
| Diisopropyl sebacate | 1.00 |
| Dimethicone copolyol | 0.25 |
| Fragrance | 1.25 |

*Weight % of salt in final composition. Salt is added in solubilized form as prepared in Example 1.

*Weight % of salt in final composition. Salt is added in solubilized form as prepared in Example 1.

Example 8 is prepared by a procedure analogous to the procedure used to prepare Examples 2 and 3.

| Ingredient | Wt. % |
| --- | --- |
| Propylene glycol | 92.75 |
| Al/Zr tetrachlorohydrate-gly | 3.00* |
| Dibenzylidene sorbitol | 1.30 |
| Hydroxypropyl cellulose | 0.50 |
| Na₄EDTA | 0.20 |
| Oleth-10 | 0.75 |
| PPG-10 butanediol | 0.75 |
| PPG-3 myristyl ether | 0.75 |

*Weight % of salt in final composition. Salt is added in solubilized form as prepared in Example 1.

Example 9 is prepared by a procedure analogous to the procedure used to prepare Examples 2 and 3.

We claim:

1. A clear gel cosmetic stick comprising a liquid vehicle, an antiperspirant salt dissolved in said liquid vehicle, a dibenzylidene alditol, and a co-gellant, wherein the amount of said dibenzylidene alditol comprises 0.5% to 2% by weight.

2. The cosmetic stick according to claim 1 wherein said co-gellant comprises a hydroxyalkyl cellulose.

3. The cosmetic stick according to claim 2 wherein said hydroxyalkyl cellulose comprises hydroxypropyl cellulose.

4. The cosmetic stick according to claim 1 additionally comprising a chelating agent.

5. The cosmetic stick according to claim 1 wherein said liquid vehicle comprises a polyhydric alcohol having from 3 to 6 carbon atoms and from 2 to 6 hydroxyl groups.

6. The cosmetic stick according to claim 2 wherein said liquid vehicle comprises a polyhydric alcohol having from 3 to 6 carbon atoms and from 2 to 6 hydroxyl groups.

7. The cosmetic stick according to claim 6 wherein said antiperspirant salt comprises aluminum chlorohydrate, enhanced efficacy aluminum chlorohydrate, aluminum-zirconium chlorohydrate or enhanced efficacy aluminum-zirconium chlorohydrate.

8. The cosmetic stick according to claim 7 comprising, in percent by weight, 70% to 95% of said liquid vehicle, 1% to 22% of said antiperspirant salt, 0.5% to 2% of said dibenzylidene alditol, and 0.1% to 0.5% of said hydroxyalkyl cellulose.

9. The cosmetic stick according to claim 8 wherein said dibenzylidene alditol comprises dibenzylidene sorbitol.

10. The cosmetic stick according to claim 9 wherein said liquid vehicle comprises propylene glycol.

11. The cosmetic stick according to claim 10 wherein said hydroxyalkyl cellulose comprises hydroxypropyl cellulose.

12. The cosmetic stick according to claim 1 wherein said stick has a turbidity of less than 120 NTU.

13. The cosmetic stick according to claim 12 wherein said liquid vehicle is substantially free of monohydric alcohol.

14. The cosmetic stick according to claim 12 wherein said liquid vehicle is substantially free of sodium hydroxide and potassium hydroxide.

15. The cosmetic stick according to claim 12 additionally comprising a chelating agent.

16. The cosmetic stick according to claim 12 additionally comprising less than 3% of one or more emollients.

17. The cosmetic stick according to claim 12 which has a hardness of 60 to 150.

* * * * *